(12) United States Patent
Daly et al.

(10) Patent No.: US 6,331,648 B1
(45) Date of Patent: Dec. 18, 2001

(54) ETHER AMINES AND DERIVATIVES

(75) Inventors: Thomas J. Daly, Barrington, IL (US); Michael Clumpner, Delayan, WI (US); Anthony J. O'Lenick, Jr., Dacula, GA (US)

(73) Assignee: Nova Molecular Technologies INC, Jonesville, WI (US)

( * ) Notice: Subject to any disclaimer, the term of this patent is extended or adjusted under 35 U.S.C. 154(b) by 0 days.

(21) Appl. No.: 09/566,505

(22) Filed: May 8, 2000

Related U.S. Application Data

(63) Continuation of application No. 09/459,562, filed on Dec. 13, 1999, now Pat. No. 6,114,585.
(51) Int. Cl.[7] .................................................. C07C 217/28
(52) U.S. Cl. ........................ 564/285; 564/287; 564/292; 564/443; 564/505
(58) Field of Search .................................. 564/443, 505, 564/285, 287, 292

(56) References Cited

U.S. PATENT DOCUMENTS 4,650,865 * 3/1987 Lange et al. ...................... 544/174
5,070,202    12/1991 Herkes .
5,616,811 * 4/1997 Vipond et al. ..................... 564/505

* cited by examiner

Primary Examiner—Sreeni Padmanabhan
Assistant Examiner—Brian J. Davis

(57) ABSTRACT

The present invention relates to a series of derivatives of novel ether amine compounds prepared by the cyanobutylation reaction of an alcohol having 3 to 22 carbon atoms with 2-pentenenitrile to form a branched alkyl ether nitrile. The alkyl ether nitrites formed by the process are hydrogenated to form alkylether amines. The resulting product can be reacted with 2-pentenenitrile and or acrylonitrile and in a subsequent step, hydrogenated to yield a diamine. Specifically, the present invention deals with two types of tertiary amines one made by the reaction of novel ether amine compounds with ethylene oxide, propylene oxide or butylene oxide or mixtures thereof producing alkoxylated tertiary amines and the other made by the reaction of novel ether amine compounds with formaldehyde and hydrogen producing methylated tertiary amines. The invention also discloses novel amine oxides, and quaternary compounds made from said tertiary amines.

22 Claims, No Drawings

ETHER AMINES AND DERIVATIVES

RELATED APPLICATIONS

This application is a continuation in part of application Ser. No. 459,562 filed Dec. 13, 1999, now U.S. Pat. No. 6,114,585.

FIELD OF THE INVENTION

The present invention relates to a series of derivatives of novel ether amine compounds prepared by the cyanobutylation reaction of an alcohol having 3 to 22 carbon atoms with 2-pentenenitrile to form a branched alkyl ether nitrile. The alkyl ether nitrites formed by the process are hydrogenated to form alkylether amines. The resulting product can be reacted with 2-pentenenitrile or acrylonitrile and hydrogenated to yield a diamine, which can likewise be derivatized. Specifically, the present invention deals with two types of tertiary amines one made by the reaction of novel ether amine compounds with ethylene oxide, propylene oxide, butylene oxide or mixtures thereof producing alkoxylated tertiary amines and the other conveniently made by the reaction of novel ether amine compounds with formaldehyde and hydrogen producing methylated tertiary amines. The invention also discloses novel amine oxides, and quaternary compounds made from said tertiary amines.

BACKGROUND OF THE INVENTION

U.S. Pat. Nos. 4,260,556 and 4,211,725 teach reaction of 2-pentenenitrile with ammonia or ethylenediamine to produce alkylaminonitriles. U.S. Pat. No. 4,496,474 teaches the reaction of 2-pentenenitrile with alkylamines having from 8 to 22 carbons to produce the corresponding nitrile compound. U.S. Pat. No. 5,070,202 teaches a process having improved reaction rate and selectivity in the reaction of 2-pentenenitrile with amines to form alkylaminonitriles by the incorporation of from 15 to 60 weight percent water in the reaction mixture. These references do not include the critical ether linkage needed to make the products of the present invention.

U.S. Pat. No. 5,902,883 to Herkes discloses the cyanobutylation of various ainines to make diamines. Herkes uses 3-pentenenitrile, 4-pentenenitrile or mixtures of 3-pentenenitrile and 4-pentenenitrile to make his product. This does not result in the desired branching that comes from the compounds of the present invention, nor does it include the critical ether linkage in the molecule. Herkes has done some work with the cyanobutylation of lower molecular weight alcohols (C3 to C8) to form primary amines. These materials lack the hydrophobicity to be good surface-active agents.

It has now been found that by reacting alcohols with 2-pentenenitrile and hydrogenating to the alkyloxypentyl amines, followed by alkoxylation or methylation to form tertiary amines and in a subsequent step derivitization of said tertiary amines results in products with unique properties. Further reaction to form the salts, quaternary salts, or amine oxides also result in products with unique properties. These include (a) superior liquidity of the resulting products, (b) improved surfactant properties and (c) improved solubility in hydrocarbons. All of these will become clear as one reads the teachings of the present invention.

SUMMARY OF THE INVENTION

The present invention relates to a series of derivatives of novel ether amine compounds prepared by the cyanobutylation reaction of an alcohol having 3 to 22 carbon atoms with 2-pentenenitrile to form a branched alkyl ether nitrile. The alkyl ether nitriles formed by the process are hydrogenated to form alkylether amines. The resulting product can be reacted with 2-pentenenitrile and or acrylonitrile and in a subsequent step, hydrogenated to yield a polyamine. The ether amine compounds used as raw materials for the preparation of the derivatives of the current invention are the topic of co-pending application Ser. No. 459,562 filed Dec. 13, 1999 incorporated herein by reference. Specifically, the present invention deals with two types of tertiary amines. One made by the reaction of novel ether amine compounds with ethylene oxide, propylene oxide, butylene oxide or mixtures thereof to produce an alkoxylated tertiary amine, and the other conveniently made by the reaction of novel ether amine compounds with formaldehyde and hydrogen to produce a methylated tertiary amine. The invention also discloses novel amine oxides, amine salts and quaternary compounds made from said tertiary amines.

Raw Material Amine Preparation

The ether amine compounds used as raw materials for the preparation of the derivatives of the current invention are the topic of co-pending application Ser. No. 459,562 filed Dec. 13, 1999 incorporated herein by reference. They conform to the following structure;

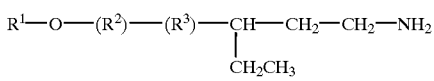

$R^1$ is selected from the group consisting of alkyl having 3 to 22 carbon atoms, $R^2$ is $-(CH_2CH_2O)_a-(CH_2CH(CH_3)O)_b(CH_2CH(CH_2CH_3)O)_c-$ a, b and c are independently integers ranging from 0 to 30,

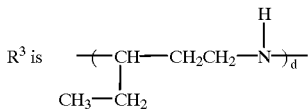

d is 0 or 1.

Class 1: Ether monoamine (d=0)

The ether monoamines conform to the following structure:

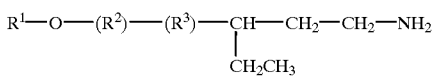

wherein;

$R^1$ is selected from the group consisting of alkyl having 3 to 22 carbon atoms $R^2$ is $-(CH_2CH_2O)_a-(CH_2CH(CH_3)O)_b-(CH_2CH(CH_2CH_3)O)_c-$;

a, b and c are independently integers ranging from 0 to 30,

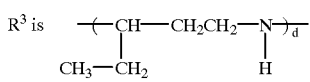

d is 0.

Class 2: Ether diamine (d=1)

Ether diamine compounds of the present invention conform to the following structure:

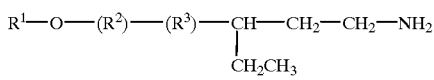

$R^1$ is selected from the group consisting of alkyl having 3 to 22 carbon atoms $R^2$ is $—(CH_2CH_2O)_a—(CH_2CH(CH_3)O)_b—(CH_2CH(CH_2CH_3)O)_c—$;

a, b and c are independently integers ranging from 0 to 30,

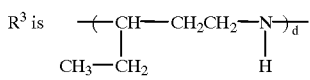

d is 1.

RAW MATERIALS ALCOHOLS

The alcohols and alcohol alkoxylates used in the manufacture of the products of the present invention are well known in the art and are commercially available from a variety of suppliers. Suppliers of these materials include Shell Chemical Company, Condea-Vista, Exxon Chemical Company, Henkel Corporation and Siltech Corporation.

$R^1O\ R^2—H$ where $R^2(CH_2CH_2O)_a—(CH_2CH(CH_3)O)_b—(CH_2CH(CH_2CH_3)O)_c$

| | | $R^2$ | |
|---|---|---|---|
| Example | $R^1$ | a | b | c |
| 1 | $C_{12}H_{25}$ | 0 | 0 | 0 |
| 2 | $C_3H_7$ | 0 | 5 | 0 |
| 3 | $C_8H_{17}$ | 0 | 0 | 0 |
| 4 | $C_{10}H_{21}$ | 0 | 0 | 0 |
| 5 | $C_{13}H_{27}$ | 0 | 0 | 0 |
| 6 | Hydrogenated Tallow 40% $C_{16}H_{33}$ & 60% $C_{18}H_{37}$ | 0 | 0 | 0 |
| 7 | Behenyl 30% $C_{20}H_{41}$ & 70% $C_{22}H_{45}$ | 0 | 0 | 0 |
| 8 | $C_{12}H_{25}$ | 30 | 0 | 0 |
| 9 | $C_8H_{17}$ | 1 | 30 | 2 |
| 10 | $C_{13}H_{27}$ | 0 | 0 | 30 |

Procedure

Preperation of Ether Nitrile (Cyanobutylation)

One mode of base alcohol is charged to a reaction flask and one mole plus approximately 10% excess of the 2-pentenenitrile is placed in an addition flask. Material is heated while stirred to a temperature of about 40° C. Base catalyst (KOH) is added based on the total weight of the rectants charged at about a 0.1 to 0.5% or more preferably 0.2–0.3% basis. A nitrogen blanket is applied to the headspace of the reaction vessel and the mixture is stirred for about 15 minutes at 40° C. to incorporate the catalyst into the alcohol. Keep the reaction flask headspace blanketed with nitrogen throughout the entire reaction period.

The addition of the 2-pentenenitrile is exothermic. Charge the 2-pentenentrile to the reaction vessel such that the temperature of reaction is maintained at 40–65° C., more preferably 45–60° C., and most preferably 50–55° C. When all of the 2-pentenenitrile has been added let react for 2 hours at 50° C. After the 2 hours add an equivalent amount of acid to neutralize the base catalyst. Stir mixture for 15 minutes then filter the 3-alkoxy-3-ethylpropylnitrile to be hydrogenated to remove salts formed on neutralization of the KOH.

Hydrogenation of 3-alkoxy-3 Ethylpropylnitrile

Charge the ether nitrile to an autoclave that is capable of operating at pressures up to 600 psig. Charge 2% by weight of Raney® Nickel (based upon the weight of the alcohol to the vessel). Seal autoclave and start agitation, increase heat to about 80 to 100° C. and vacuum strip out any water that may have been introduced during cyanobutylation or from Raney® nickel. When no more water appears on the condenser of the vacuum set-up, close autoclave and charge hydrogen gas to about 5 psig. Charge ammonia to vessel to about 60 to 70 psig. Increase heat to 135° C. and note pressure. Add hydrogen such that about 150 to 200 psig additional pressure is measured on the autoclave pressure gauge. Maintain continuous hydrogen addition in this manner for a period of 4–6 hours, then close the hydrogen inlet valve and note pressure on the pressure gauge. Turn off heat and cool to about 70° C. Carefully, open vent to release pressure and vacuum strip to remove ammonia. Discharge the 3-alkoxy-3ethylpropylamine and filter to remove Raney® nickel catalyst.

Example 11

Preparation of 3-dodecoxy-3-ethylpropylnitrile (Cyanobutylation)

To a 500 ml round bottomed flask fitted with a mechanical stirrer, gas inlet tube and dropping funnel was added 186 g (1 mole) of n-dodecyl alcohol (Example 1) and 0.7 g of KOH. A nitrogen blanket was maintained throughout the procedure. The temperature was increased to 40° C. while stirring to dissolve and disperse the KOH. The dropping funnel was charged with 90.0 g of 2-pentenenitrile (1.11 mole). The nitrile was added with stirring at a rate that kept the reaction temperature from rising over 50° C. After the addition the reaction was allowed to proceed for an additional 2 hours at 50° C. The catalyst, KOH, was then deactivated by neutralization with an equivalent amount of acetic acid. After neutralization the mixture was stirred for 15 minutes and then filtered to remove the salts that formed on neutralization. The excess 2-pentenenitrile was then removed by vacuum stripping.

Example 12–20

Example 11 is repeated, only this time replacing the alcohol example with the type and quantity of alcohol shown.

| ether nitrile | Alcohol | | KOH (95%) |
|---|---|---|---|
| Example | Example | Grams | Grams |
| 12 | 2 | 350.0 | 1.0 |
| 13 | 3 | 130.0 | 0.5 |
| 14 | 4 | 158.0 | 0.5 |
| 15 | 5 | 200.0 | 0.6 |
| 16 | 6 | 259.0 | 0.7 |
| 17 | 7 | 318.0 | 0.8 |
| 18 | 8 | 1506.0 | 3.8 |
| 19 | 9 | 2054.0 | 5.0 |
| 20 | 10 | 2360.0 | 6.0 |

Example 21

Preperation of 3-dodecyloxy-3-ethylpropylamine

The 265 grams (0.99) of 3-dodecyloxy-3-ethylpropylnitrile was poured into a suitable sized autoclave equipped with stirring. Raney® nickel, 5.3 g was also added. After sealing the autoclave and heating to 80° C. a vacuum was applied while stirring to remove water introduced with the catylyst. When no more water appeared on the condenser of the vacuum set-up the vacumn was released and hydrogen was allowed to fill the vessel to a pressure of 5 psig. Ammonia was then added until the pressure rose to 65 psig. The temperature was then increased to 135° C. that caused the pressure to rise to about 150 psig. The pressure was then increased to 400 psig with hydrogen and the stirring speed increased to 1200 rpm. After 4 hours the valve to the hydrogen cylinder was closed and the pressure in the headspace monitored. Since the pressure dropped by 100 psig over the next 15 minutes, the valve was opened again and the reaction allowed to proceed for another hour. After checking for a pressure drop again, none was noted over the next 15 minutes and the reaction was declared complete. The heat was turned off and cooling water run through the coils until the temperature dropped to 70° C. After venting off the hydrogen and flushing with nitrogen, residual ammonia was vacuum stripped. The product, 3-n-dodecoxy-3-ethylpropylamine, was filtered to remove Raney® nickel catalyst. The yield was essentially quantitative.

Example 21 is repeated, only this time replacing the ether monoamine of example 12 with the type and quantity of monoether amine shown.

| Ether Mono Amine | ether nitrile | |
|---|---|---|
| Example | Example | Grams |
| 22 | 12 | 435.0 |
| 23 | 13 | 215.0 |
| 24 | 14 | 243.0 |
| 25 | 15 | 285.0 |
| 26 | 16 | 344.0 |
| 27 | 17 | 403.0 |
| 28 | 18 | 1591.0 |
| 29 | 19 | 2139.0 |
| 30 | 20 | 2445.0 |

The products are used to prepare the tertiary amines and their derivatives that are the subject of this invention.

COMPOUNDS OF THE PRESENT INVENTION

The introduction of the ether group into the molecule together with the specific ethyl branching introduced by using 2-pentenenitrile results in a product having superior liquidity. Liquidity is a property desirable in many applications. There are not many options available to improve liquidity. The material with the highest melting point in a series is the fully saturated product. One way to improve liquidity is to introduce unsaturation. This is why oleyl products with one double bond are much more liquid than stearyl products that have the same number of carbon atoms but no double bonds. The difficulty here is that double bonds are susceptible to a process known as rancidity. This process breaks the double bond and forms aldehydic components that are not only reactive with each other, but also have mal odor and mal taste. This instability limits the utility of unsaturated materials in many applications. We have found that improved liquidity is achieved by introduction of the ether group and the branching found in the 2-pentenenitrile. Standard ether amines that are made with acrylonitrile result in linear materials that do not have the same degree of improved liquidity as the ether amines that are derived from using 2-pentenenitrile in place of acrylonitrile. Additionally, the products can be formulated at higher % actives. The introduction of the branching allows for improved solvency, and ease of formulation and use as hair conditioners, fabric softeners, herbicide adjuvants/surfactants, fuel additives, etc.

DETAILED DESCRIPTION

The present invention relates to a series of derivatives of novel ether amine compounds prepared by the cyanobutylation reaction of an alcohol having 3 to 22 carbon atoms with 2-pentenenitrile to form a branched alkyl ether nitrile. The alkyl ether nitrites formed by the process are hydrogenated to form alkylether amines. Specifically, the present invention deals with two types of tertiary amines, one made by the reaction of novel ether amine compounds with ethylene oxide, propylene, butylene oxide or mixtures thereof producing alkoxylated tertiary amines and the other conveniently made by the reaction of novel ether amine compounds with formaldehyde and hydrogen producing methylated tertiary amines. The invention also discloses novel amine oxides and quaternary compounds made from said tertiary amines.

Class 1: Monoether amine (d=0)

Preparation of Tertiary Amines

1. Preparation of the Alkoxylated Tertiary Ether Amine

General Procedure

Step 1.

The specified amount (1 mole) of the alkyloxypentyl amine (Examples 21–30) is charged into an appropriately sized autoclave. The reactor is purged with nitrogen. Alkylene oxide is then reacted at 130–140° C. Approximately 2 hours is required for addition of the alkylene oxide. The reaction mixture is held at 130–140° C. for 2 hours, with stirring. Cool to 70° C. then vent for 10 minutes. Then vacuum strip at 15 to 28 inches of mercury for 30 minutes. The product corresponded to alkoxylated amine.

It should be clearly understood by those skilled in the art that at a mole ratio of one alcohol to one pentenenitrile, there is some small amount of unreacted alcohol in the product mixture. In most cases this is not undesirable. The mole ratios can be adjusted to produce the desired products.

Step 2.

To the product from the first step was added 0.2 to 0.5% by weight of 45% potassium hydroxide (based upon the total batch weight). By using both vacuum and nitrogen stripping the water level was brought down to below 0.1% by weight. The autoclave was then closed and heated to 110 to 115° C. The specified amount of alkylene oxide (ethylene oxide, propylene oxide, or combinations thereof) is then added at a rate of one mole per hour. Once all the alkylene oxide has been added the batch is held at constant temperature for two hours. The product is cooled down to 70° C. and vacuum strip at 15 to 28 inches of mercury for thirty minutes. The product is then filtered. The product is the alkoxylated amine with the required number of moles of alkylene oxide.

Examples 31–40

| Alkoxylated Tertiary Amine | Ether Mono Amine Compound | Ethylene Oxide | Propylene oxide |
|---|---|---|---|
| Example | Example | Grams | Grams | Grams |
| 31 | 21 | 271.0 | 220.0 | 0.0 |
| 32 | 22 | 435.0 | 0.0 | 116.0 |
| 33 | 23 | 215.0 | 88.0 | 0.0 |
| 34 | 24 | 243.0 | 2,640.0 | 0.0 |
| 35 | 25 | 285.0 | 0.0 | 116.0 |
| 36 | 26 | 344.0 | 88.0 | 0.0 |
| 37 | 27 | 403.0 | 0.0 | 1160.0 |
| 38 | 28 | 1591.0 | 440.0 | 580.0 |
| 39 | 29 | 2139.0 | 44.0 | 116.0 |
| 40 | 30 | 2445.0 | 0.0 | 116.0 |

The tertiary amine compounds so prepared are referred to herein as alkoxylated tertiary ether amines and conform to the following structure:

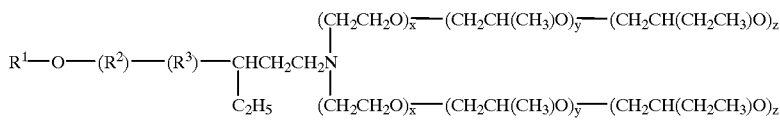

$R^1$ is selected from the group consisting of alkyl having 3 to 22 carbon atoms, aryl having 6 to 20 carbon atoms;

$R^2$ is $-(CH_2CH_2)_a-(CH_2CH(CH_3)O)_b-(CH_2CH(CH_2CH_3)O)_c-$ a, b and c are independently integers ranging from 0 to 30, with the proviso that a+b+c are a minimum of 0 and a maximum of 60;

$R^3$ is

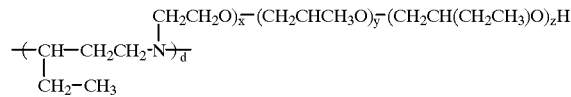

d is 0;

x, y and z are integers each ranging 0 to 30 with the proviso that x+y+z is a minimum of 2 and a maximum of 60.

2. Preperation of Tertiary Amine —N,N-Dimethyl-pentylamines

General Procedures

In a suitably sized autoclave is charged (1 mole) of the specified amine (examples 21–30) and 0.5% by weight (based upon the weight of the amine) of a nickel catalyst G-49-B. Next add 0.5% by weight (based upon the weight of the amine) of filter aid. Next add 0.5% by weight (based upon the weight of the formalin) of $NaH_2PO_4$. The contents of the autoclave is then heated to 150° C. Hydrogenis then applied to a pressure of 100 psig, with continuous hydrogen flow and continuous hydrogen venting. Next, 2.1 moles of formaldehyde (162.2 grams) is added as Formalin (37% formaldeyde) at a rate of 0.85 ml per minute. After the addition is complete the batch is held for 30 minutes. The reaction mass is cooled to 80° C. and vented to atmospheric pressure. The product is then filtered as it is discharged from the autoclave. The product is the desired N,N-dimethyl-pentylamine.

Example 41–50

| Dimethyl Tertiary Amine | Ether Mono Amine Compound | |
|---|---|---|
| Example | Example | Grams |
| 41 | 21 | 271.0 |
| 42 | 22 | 435.0 |
| 43 | 23 | 215.0 |
| 44 | 24 | 243.0 |
| 45 | 25 | 285.0 |
| 46 | 26 | 344.0 |
| 47 | 27 | 403.0 |
| 48 | 28 | 1591.0 |
| 49 | 29 | 2139.0 |
| 50 | 30 | 2445.0 |

The tertiary amine compounds so prepared are referred to herein as methylated tertiary ether amines and conform to the following structure:

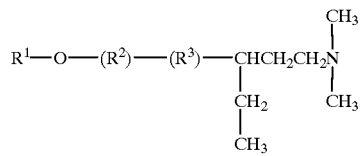

$R^1$ is selected from the group consisting of alkyl having 3 to 22 carbon atoms, aryl having 6 to 20 atoms;

$R^2$ is $-(CH_2CH_2O)_a-CH(CH_3)O)_b-(CH_2CH(CH_2CH_3)O)_c-$ a,b and c are independently integers ranging from 0 to 30, with the proviso that a+b+c are a minimum of 0 and a maximum of 60;

$R^3$ is 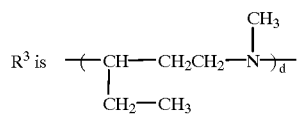

d is 0.

Preparation of Tertiary Amine Derivatives

1. Preparation of the Methyl Chloride Quaternary Compound

General Procedure

In a suitable sized stainless Parr autoclave was added one mole of tertiary amine (examples 31–50), 1% sodium bicarbonate (based upon the weight of the tertiary amine), and isopropanol (based upon the desired activity and viscosity). The autoclave is sealed, agitation applied and a nitrogen purge applied. The temperature is raised to 85° C. Charge 1.2 moles (61.0 grams) of methyl chloride slowly, so that the temperature is maintained between 80 and 90° C. After all the methyl chloride is added keep the temperature at 80° C. for two hours under agitation. Cool down and filter. The product is used without additional purification.

Examples 51–61

| Methyl Chloride Quat Example | Tertiary Amine Compound Example | Grams | Isopropanol Grams |
|---|---|---|---|
| 51 | 31 | 491.0 | 160.0 |
| 52 | 33 | 303.0 | 100.0 |
| 53 | 35 | 401.0 | 125.0 |
| 54 | 36 | 432.0 | 400.0 |
| 55 | 41 | 298.0 | 100.0 |
| 56 | 42 | 463.0 | 0.0 |
| 57 | 44 | 271.0 | 75.0 |
| 58 | 45 | 313.0 | 100.0 |
| 59 | 46 | 372.0 | 300.0 |
| 60 | 47 | 431.0 | 450.0 |
| 61 | 48 | 1619.0 | 3500.0 |

2. Preparation of Methyl Sulfate Quaternary Compound

General Procedure

In a four-necked round bottom flask containing a thermometer, mechanical stirrer, condenser and dropping funnel was added 1 mole of tertiary amine (examples 31–50) and isopropanol (based upon the desired activity of the final quaternary compound) and 3% water (based upon the tertiary amine weight). The contents were heated with stirring to 70° C. while adding 0.95 moles of dimethylsulfate (126.0 grams) from the dropping funnel over 1 hour. The mixture was stirred at 70° C. for 1 hour after the addition was complete. The desired alkoxypentylammonium methylsulfate compound was cooled and filtered.

| Methyl Sulfate Quat Example | Tertiary Amine Example | Grams | Isopropanol Grams |
|---|---|---|---|
| 62 | 31 | 491.0 | 160.0 |
| 63 | 33 | 303.0 | 100.0 |
| 64 | 34 | 2883.0 | 2800.0 |
| 65 | 35 | 401.0 | 125.0 |
| 66 | 36 | 432.0 | 400.0 |
| 67 | 41 | 298.0 | 100.0 |
| 68 | 42 | 463.0 | 125.0 |
| 69 | 44 | 271.0 | 75.0 |
| 70 | 46 | 372.0 | 300.0 |
| 71 | 47 | 431.0 | 450.0 |

3. Preperation of Benzyl Chloride Quaternery Compound

General Procedure

In a suitable four-necked round bottom flask equipped with a thermometer, condenser, dropping funnel and mechanical stirrer was added one mole of tertiary amine (examples 31–50). Next add, 1% by weight of sodium bicarbonate (based upon the weight of the tertiary amine), 3% by weight of water (based upon the weight of the tertiary amine), and isopropanol (based upon the desired activity and viscosity of the final quaternary compound). Stir and heat to 80–85° C., under a nitrogen blanket. Add one mole of benzyl chloride (127.0 grams), while maintaining the temperature in the range of 80–85° C. After the addition is complete, hold the contents at 80–85° C. for two hours. Cool the contents and filter. The product is used without additional purification.

| Benzyl Chloride Quat Example | Tertiary amine Example | Grams | Isopropanol Grams |
|---|---|---|---|
| 72 | 31 | 491.0 | 160.0 |
| 73 | 34 | 2883.0 | 2800.0 |
| 74 | 36 | 432.0 | 400.0 |
| 75 | 37 | 1563.0 | 350.0 |
| 76 | 38 | 2611.0 | 2500.0 |
| 77 | 39 | 2241.0 | 750.0 |
| 78 | 41 | 299.0 | 100.0 |
| 79 | 43 | 243.0 | 30.0 |
| 80 | 45 | 313.0 | 100.0 |
| 81 | 49 | 2167.0 | 700.0 |

4. Preperation of Amine Oxide

General Procedure

In a suitable four-necked round bottom flask equipped with a stirrer, dropping funnel and a thermometer, is added 1.0 mole of the specified tertiary amine (examples 31–50). Next is added water or isopropanol to make the desired activity and viscosity of the amine oxide. The mixture was stirred and slowly heated to 65° C. 102.0 grams of 35% hydrogen peroxide (1.05 moles of $H_2O_2$) is added dropwise keeping the temperature between 70–75° C. The rate of addition is determined by the exotherm, keeping the temperature of the reaction in the specified range. After the addition, the reaction was held at 70–75° C. for 2 hours. The amine oxide is obtained and utilized without purification.

| Amine Oxide Example | Tertiary Amine Compound Example | Grams | Water Grams | Isopropanol Grams |
|---|---|---|---|---|
| 81 | 31 | 491.0 | 1500.0 | 0.0 |
| 82 | 32 | 551.0 | 0.0 | 500.0 |
| 83 | 33 | 303.0 | 0.0 | 300.0 |
| 84 | 35 | 401.0 | 0.0 | 350.0 |
| 85 | 37 | 1563.0 | 0.0 | 1500.0 |
| 86 | 40 | 2560.0 | 0.0 | 2500.0 |
| 87 | 41 | 299.0 | 600.0 | 0.0 |
| 88 | 44 | 271.0 | 500.0 | 0.0 |
| 89 | 46 | 372.0 | 1100.0 | 0.0 |
| 90 | 47 | 431.0 | 1200.0 | 0.0 |
| 91 | 50 | 2473.0 | 0.0 | 2300.0 |

The first type of ether amine derivatives are based upon alkoxylated tertiary amines and conform to the following structure;

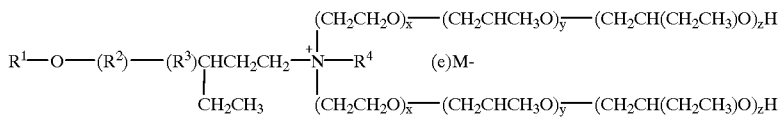

$R^1$ is selected from the group consisting of alkyl having 3 to 22 carbon atoms, aryl having 6 to 20 carbon atoms;

$R^2$ is —$(CH_2CH_2O)_a$—$(CH_2CH(CH_3)O)_b$—$(CH_2CH(CH_2CH_3)O)_c$— a, b and c are independently integers ranging from 0 to 30, with the proviso that a+b+c are a minimum of 0 and a maximum of 60;

$R^3$ is

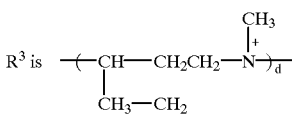

d is 0;

$R^4$ is selected from the group consisting of $CH_3$—, O, H, methyl phenyl;

x, and y and z are integers each ranging 0 to 30 with the proviso that x+y+z is a minimum of 2 and a maximum of 60;

e is an integer needed for charge balance and ranges from 0 to 2; and

M is an anion selected from a group of appropriate anions such as Cl, Br, $CH_3SO_4$, and $CH_3C(O)O$.

The second type of ether amine derivatives are based upon methylated tertiary amines and conform to the following structure;

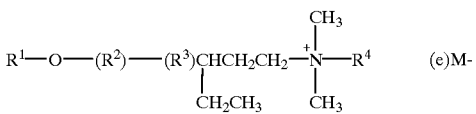

$R^1$ is selected from the group consisting of alkyl having 3 to 22 carbon atoms, aryl having 6 to 20 carbon atoms;

$R^2$ is —$(CH_2CH_2O)_a$—$(CH_2CH(CH_3)O)_b$—$(CH_2CH(CH_2CH_3)O)_c$— a, b and c are independently integers ranging from 0 to 30, with the proviso that a+b+c are a minimum of 0 and a maximum of 60;

$R^3$ is

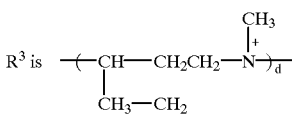

d is 0;

$R^4$ is selected from the group consisting of $CH_3$—, O, H, methyl phenyl;

e is an integer needed for charge balance and ranges from 0 to 2; and

M is an anion selected from a group of appropriate anions such as Cl, Br, $CH_3SO_4$, and $CH_3C(O)O$.

Within each type of tertiary amine derivatives (those based upon alkoxylated tertiary amines and those based upon methylated tertiary amines) are two classes of compounds and several sub classes of compounds embodied within the generic structure. The present invention deals with derivatives based upon mono amines (i.e. d=0).

PREFERRED EMBODIMENT

In a preferred embodiment the ether amine derivative conforming to the following structure:

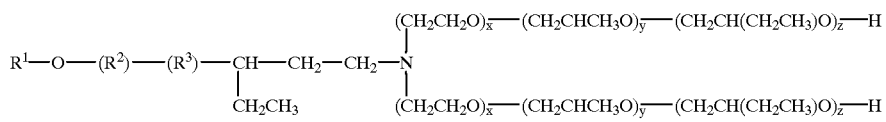

R¹ is selected from the group consisting of alkyl having 3 to 22 carbon atoms, aryl having 6 to 20 carbon atoms;

R² is —(CH₂CH₂O)ₐ—(CH₂CH(CH₃)O)ᵦ—(CH₂CH(CH₂CH₃)O)ᶜ— a, b and c are independently integers ranging from 0 to 30, with the proviso that a+b+c are a minimum of 0 and a maximum of 60;

R³ is

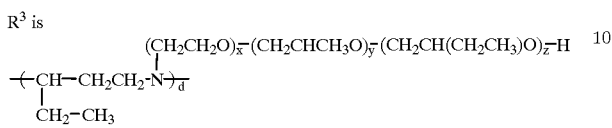

d is 0;

x, y and z are integers each ranging 0 to 30 with the proviso that x+y+z is a minimum of 2 and a maximum of 60.

In a preferred embodiment the ether amine derivatives conforming to the following structure;

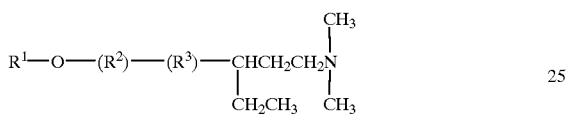

R¹ is selected from the group consisting of alkyl having 3 to 22 carbon atoms, aryl having 6 to 20 carbon atoms;

R² is —(CH₂CH₂O)ₐ—(CH₂CH(CH₃) O)ᵦ—(CH₂CH(CH₂CH₃)O)ᶜ— a, b and c are independently integers ranging from 0 to 30, with the proviso that a+b+c are a minimum of 0 and a maximum of 60;

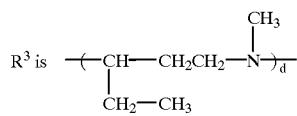

d is 0.

In a preferred embodiment the ether amine derivative conforming to the following structure;

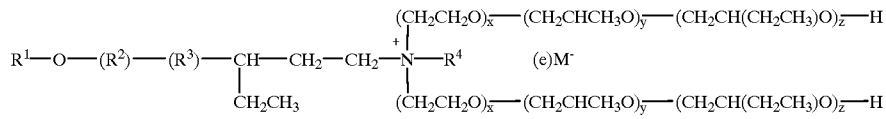

R¹ is selected from the group consisting of alkyl having 3 to 22 carbon atoms, aryl having 6 to 20 carbon atoms;

R² is —(CH₂CH₂O)ₐ—(CH₂CH(CH₃) O)ᵦ—(CH₂CH₂(CH₂CH₃)O)ᶜ— a, b and c are independently integers ranging from 0 to 30, with the proviso that a+b+c are a minimum of 0 and a maximum of 60;

R³ is

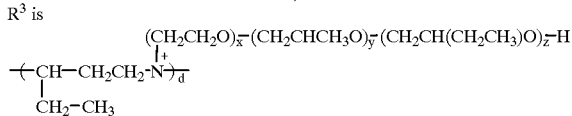

d is 0;

R⁴ is selected from the group consisting of CH₃—, O, H, methyl phenyl;

x, y and z are integers each ranging 0 to 30 with the proviso that x+y+z is a minimum of 2 and a maximum of 60;

e is an integer needed for charge balance and ranges from 0 to 2; and

M is an anion selected from a group of appropriate anions such as Cl, Br, CH₃SO₄, and CH₃C(O)O.

In a preferred embodiment the ether amine derivatives conforming to the following structure;

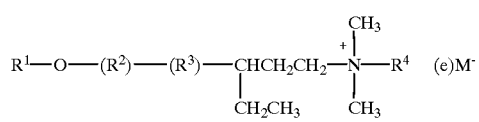

R¹ is selected from the group consisting of alkyl having 3 to 22 carbon atoms, aryl having 6 to 20 carbon atoms;

R² is —(CH₂CH₂O)ₐ—(CH₂CH(CH₃) O)ᵦ—(CH₂CH(CH₂CH₃)O)ᶜ— a, b and c are independently integers ranging from 0 to 30, with the proviso that a+b+c are a minimum of 0 and a maximum of 60;

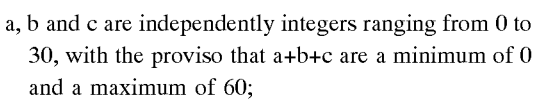

d is 0.

R⁴ is selected from the group consisting of CH₃—, O, H, methyl phenyl;

e is an integer needed for charge balance and ranges from 0 to 2; and

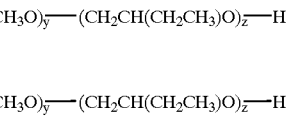

M is an anion selected from a group of appropriate anions such as Cl, Br, CH₃SO₄, and CH₃C(O)O.

In another preferred embodiment R⁴ is CH₃—.

In a preferred embodiment R⁴ is O, and e is 0.

In a preferred embodiment R⁴ is H.

In another preferred embodiment R⁴ is methyl phenyl.

In a preferred embodiment R¹ is 8 to 13 carbons, R² is O, R⁴ is O, x is 2, y and z are 0, and In a preferred embodiment R¹ is 8 to 13 carbons, where R² is 0, x is 5 and y and z are 0.

In a preferred embodiment R¹ is 8 thru 22 carbons, b is 10, c is 10, a is 0, z is 2 and x and y are 0.

In a preferred embodiment R¹ has 8–13 carbons and R² is 0.

In a preferred embodiment $R^1$ is 8 to 18 carbons, $R^2$ is 0, y is 2, x and z are 0, $R^4$ is $CH_3$ and M is Cl.

In a preferred embodiment $R^1$ is 8 to 13 carbons, $R^2$ is 0, x is 2, y and z are 0, $R^4$ is H, and M is $CH_3$ C(O)O.

In a preferred embodiment $R^1$ is 10 to 13 carbons, $R^2$ is 0, x is 2, y and z are 0, $R^4$ is O, and e is 0.

In a preferred embodiment where $R^1$ is 16 to 22 carbons and $R^2$ is 0.

In a preferred embodiment where $R^1$ is 8 to 13 carbons, $R^2$ is 0, $R^4$ is O, and e is 0.

In a preferred embodiment where $R^1$ is 8 to 13 carbons, $R^2$is 0, $R^4$ is methyl phenyl and M is Cl.

Applications Examples

The compounds of the present invention are outstanding surface-active agents (surfactants). They find applications in a variety of market segments where there is a need for high performance and cost effective products is highest. The wide variability in the exact structure of the compound allows us to make products with a tremendous range of solubilities in water, oil and other solvents. The compounds function as emulsifiers, wetting agents, conditioners, adjuvants, corrosion inhibitors and detergents. While illustrative of the type of products in which compounds of the resent invention may find applications, this list is not intended to be exhaustive or all-inclusive.

Surfactants

The alkoxylated tertiary amine compounds (examples 31 and 33), and the amine oxides and quaternaries prepared using the tertiary amines in examples 31 and 33 are outstanding adjuvant/surfactants for herbicides, most importantly glyphosate. These compounds not only give very stable formulations with outstanding wetting properties, but also allow for formulations that have higher concentrations of herbicides without the gelation problems of other surfactants.

Fabric Softener Compounds

There is a very strong interest in the formulation of liquid highly concentrated fabric softeners for use in laundry applications. The branching pattern introduced by the ethyl branch in the compounds of the present invention allows their quaternary compound derivatives to be formulated into efficacious, liquid, and highly concentrated softeners. These branched cationic materials are also quite functional as antistatic agents. Specifically, the compounds of examples 59, 60, 70 and 71 are outstanding softeners.

Fuel Additives

Compounds of the present invention find applications in fuel applications, both diesel and gasoline. While not wanting to be held to a specific method of functionality, we believe that the properly selected molecule has an affinity for the metal surface and prevents corrosion and provides outstanding detergency for the engine. The compounds are clean burning and compatible with the components of the fuel.

Specific examples of compounds of the present invention useful as fuel additives include examples 83 and 84.

Personal Care

The quaternary compounds of the present invention are mild. They provide antistatic properties, softness and shine to hair when applied as conditioners, reducing tangling. The products based upon alkoxylation technology give less build up on the hair. This suggests their use in an everyday product, where build up is a concern. A specific example of a compound of the present invention useful as a personal care hair conditioner is example 59.

Asphalt

The propoxylated amines and diamines of this invention are useful as asphalt emulsifiers and anti-stripping adhesion agents for asphalt road building.

What is claimed is:

1. An ether amine derivative conforming to the following structure:

$$R^1-O-(R^2)-CH-CH_2-CH_2-N \begin{matrix} (CH_2CH_2O)_{\overline{x}}- \\ | \\ | \\ (CH_2CH_2O)_{\overline{x}}- \end{matrix}$$

$$| \\ CH_2CH_3$$

$$-(CH_2CHCH_3O)_{\overline{y}}-(CH_2CH(CH_2CH_3)O)_{\overline{z}}-H$$

$$-(CH_2CHCH_3O)_{\overline{y}}-(CH_2CH(CH_2CH_3)O)_{\overline{z}}-H$$

$R^1$ is selected from the group consisting of alkyl having 3 to 22 carbon atoms, aryl having 6 to 20 carbon atoms;

$R^2$ is $-(CH_2CH_2O)_a-(CH_2CH(CH_3)\ O)_b-(CH_2CH(CH_2CH_3)O)_c-$ a, b and c are independently integers ranging from 0 to 30, with the proviso that a+b+c are a minimum of 0 and a maximum of 60;

x, y and z are integers each ranging 0 to 30 with the proviso that x+y+z is a minimum of 2 and a maximum of 60.

2. An ether amine derivatives conforming to the following structure;

$$R^1-O-(R^2)-CHCH_2CH_2N \begin{matrix} CH_3 \\ | \\ | \\ CH_3 \end{matrix}$$

$$| \\ CH_2CH_3$$

$R^1$ is selected from the group consisting of alkyl having 3 to 22 carbon atoms, aryl having 6 to 20 carbon atoms;

$R^2$ is $-(CH_2CH_2O)_a-(CH_2CH(CH_3)\ O)_{b13\ (CH2}CH(CH_2CH_3)O)_c-$ a, b and c are independently integers ranging from 0 to 30, with the proviso that a+b+c are a minimum of 0 and a maximum of 60.

3. An ether amine derivative conforming to the following structure;

$$R^1\text{—O—}(R^2)\text{—}\underset{\underset{CH_2CH_3}{|}}{CH}\text{—}CH_2\text{—}CH_2\text{—}\underset{}{\overset{+}{N}}\begin{matrix}(CH_2CH_2O)_{\overline{x}}\text{—}(CH_2CHCH_3O)_{\overline{y}}\text{—}(CH_2CH(CH_2CH_3)O)_{\overline{z}}\text{—}H \\ | \\ \text{—}R^4 \quad (e)M^- \\ | \\ (CH_2CH_2O)_{\overline{x}}\text{—}(CH_2CHCH_3O)_{\overline{y}}\text{—}(CH_2CH(CH_2CH_3)O)_{\overline{z}}\text{—}H \end{matrix}$$

$R^1$ is selected from the group consisting of alkyl having 3 to 22 carbon atoms, aryl having 6 to 20 carbon atoms;

$R^2$ is —$(CH_2CH_2O)_a$—$(CH_2CH(CH_3)\ O)_b$—$(CH_2CH(CH_2CH_3)O)_c$— a, b and c are independently integers ranging from 0 to 30, with the proviso that a+b+c are a minimum of 0 and a maximum of 60;

$R^4$ is selected from the group consisting of $CH_3$—, O, H, methyl phenyl;

x, y and z are integers each ranging 0 to 30 with the proviso that x+y+z is a minimum of 2 and a maximum of 60;

e is an integer needed for charge balance and ranges from 0 to 2; and

M is an anion selected from a group consisting of Cl, Br, $CH_3SO_4$, and $CH_3C(O)O$.

4. An ether amine derivative of claim 3 wherein $R^4$ is $CH_3$—.

5. An ether amine oxide of claim 3 wherein $R^4$ is O, and e is 0.

6. An ether amine derivative of claim 3 wherein $R^4$ is H.

7. An ether amine derivative of claim 3 wherein $R^4$ is methyl phenyl.

8. An ether amine derivative of claim 3 where $R^1$ is 8 to 13 carbons, $R^2$ is 0, $R^4$ is O, x is 2, y and z are 0, and e is 0.

9. An ether amine derivative of claim 1 where $R^1$ is 8 to 13 carbons, where $R^2$ is 0, x is 5 and y and z are 0.

10. An ether amine derivative of claim 1 where $R^1$ is 8 thru 22 carbons, b is 10, c is 10, a is 0, z is 2 and x and y are 0.

11. An ether amine derivative of claim 1 where $R^1$ has 8–13 carbons and $R^2$ is 0.

12. An ether amine derivative of claim 1 where $R^1$ is 8 to 18 carbons, $R^2$ is 0, y is 2, x and z are 0, $R^4$ is $CH_3$ and M is Cl.

13. An ether amine derivative of claim 3 where $R^1$ is 8 to 13 carbons, $R^2$ is 0, x is 2, y and z are 0, $R^4$ is H, and M is $CH_3\ C(O)O$.

14. An ether amine derivative of claim 3 where $R^1$ is 10 to 13 carbons, $R^2$ is 0, x is 2, y and z are 0, $R^4$ is O, and e is 0.

15. An ether amine derivatives conforming to the following structure;

$$R^1\text{—O—}(R^2)\text{—}\underset{\underset{CH_2CH_3}{|}}{CHCH_2CH_2}\text{—}\underset{\underset{CH_3}{|}}{\overset{\overset{CH_3}{|}}{\overset{+}{N}}}\text{—}R^4 \quad (e)M^-$$

$R^1$ is selected from the group consisting of alkyl having 3 to 22 carbon atoms, aryl having 6 to 20 carbon atoms;

$R^2$ is —$(CH_2CH_2O)_a$—$(CH_2CH(CH_3)\ O)_b$—$(CH_2CH(CH_2CH_3)O)_c$— a, b and c are independently integers ranging from 0 to 30, with the proviso that a+b+c are a minimum of 0 and a maximum of 60;

$R^4$ is selected from the group consisting of $CH_3$—, O, H, methyl phenyl;

e is an integer needed for charge balance and ranges from 0 to 2; and

M is an anion selected from a group consisting of Cl, Br, $CH_3SO_4$, and $CH_3C(O)O$.

16. An ether amine derivative of claim 15 wherein $R^4$ is $CH_3$—.

17. An ether amine oxide of claim 15 wherein $R^4$ is O, and e is 0.

18. An ether amine derivative of claim 15 wherein $R^4$ is H.

19. An ether amine derivative of claim 15 wherein $R^4$ is methyl phenyl.

20. An ether amine derivative of claim 15 where $R^1$ is 16 to 22 carbons and $R^2$ is 0.

21. An ether amine oxide of claim 15 where $R^1$ is 8 to 13 carbons, $R^2$ is 0, $R^4$ is O, and e is 0.

22. An ether amine derivative of claim 15 where $R^1$ is 8 to 13 carbons, $R^2$ is 0, $R^4$ is methyl phenyl and M is Cl.

* * * * *